US011406613B2

(12) United States Patent
Sofat

(10) Patent No.: US 11,406,613 B2
(45) Date of Patent: Aug. 9, 2022

(54) TREATMENT OF OSTEOARTHRITIS

(71) Applicant: ST GEORGE'S HOSPITAL MEDICAL SCHOOL, London (GB)

(72) Inventor: Nidhi Sofat, London (GB)

(73) Assignee: ST. GEORGE'S HOSPITAL MEDICAL SCHOOL, London (GB)

( * ) Notice: Subject to any disclaimer, the term of this patent is extended or adjusted under 35 U.S.C. 154(b) by 0 days.

(21) Appl. No.: 16/339,607

(22) PCT Filed: Oct. 9, 2017

(86) PCT No.: PCT/GB2017/053051
§ 371 (c)(1),
(2) Date: Apr. 4, 2019

(87) PCT Pub. No.: WO2018/069687
PCT Pub. Date: Apr. 19, 2018

(65) Prior Publication Data
US 2019/0240175 A1 Aug. 8, 2019

(30) Foreign Application Priority Data
Oct. 13, 2016 (GB) ..................... 1617380

(51) Int. Cl.
A61K 31/197 (2006.01)
A61P 19/02 (2006.01)
(52) U.S. Cl.
CPC ............ A61K 31/197 (2013.01); A61P 19/02 (2018.01)
(58) Field of Classification Search
CPC .............................. A61K 31/197; A61P 19/02
See application file for complete search history.

(56) References Cited

U.S. PATENT DOCUMENTS 6,127,418 A    10/2000 Bueno et al.
6,329,429 B1   12/2001 Schrier et al.

FOREIGN PATENT DOCUMENTS

EP    0934061       5/2003
WO    WO 98/03167   1/1998
WO    WO 98/58641   12/1998

OTHER PUBLICATIONS

Widerstrom-Noga et al., PAIN 154, 2013, 204-212.*
Altman et al., The American College of Rheumatology Criteria for the Classification and Reporting of Osteoarthritis of the Hand, *Arthritis & Rheumatism*, 1990, 33(11):1601-1610.
Anonymous: "Pain Management in Osteoarthritis Using the Centrally Acting Analgesics Duloxetine and Pregabalin" NCT02612233 ClinicalTrials.gov Archive, 2016.
Basoski et al., "Efficacy of Hydroxychloroquine in Primary hand Osteoarthritis: A randomized, double-blind, placebo controlled trial," *Ann. Rhem. Dis., Scientific Abstracts*, 2015, p. 188.
Bellamy et al., "Development of multinational Definitions of Minimal Clinically Important improvement and Patient Acceptable Symptomatic State in Osteoarthritis," *Arthritis Care & Research*, 2015, 67(7):972-980.
Bjelland et al., "The validity of the Hospital Anxiety and Depression Scale. An updated literature review," *Journal of Psychosomatic Research*, 2002, 52:69-77.
Bmyere et al., "Can We Identify Patients with High Risk of Osteoarthritis Progression Who Will Respond to Treatment? A Focus on Epidemiology and Phenotype of Osteoarthritis," *Drugs Aging*, 2015, 32:179-187.
Chappell et al., "Duloxetine, a centrally acting analgesic, in the treatment of patients with osteoarthritis knee pain: A 13-week, randomized, placebo-controlled trial," *PAIN*, 2009, 146:253-260.
Da Costa et al., "Effectiveness of non-steroidal anti-inflammatory drugs for the treatment of pain in knee and hip osteoarthritis: a network meta-analysis", *Lancet*, 2016, 387:2093-2105.
Davis et al., "Are Bisphosphonates Effective in the Treatment of Osteoarthritis Pain? A Meta-Analysis and Systematic Review," *PLoS ONE*, 2013, 8(9):e72714.
International Search Report and Written Opinion issued in Corresponding International Patent Application No. PCT/GB2017/053051, dated Nov. 22, 2017.
Kellgren & Lawrence, "Radiological Assessment of Osteo-Arthrosis" *Ann. Rhem. Dis.*, 1957, 16:494-502.
Kingsbury et al., "Pain reduction with oral methotrexate in knee osteoarthritis, a pragmatic phase iii trial of treatment effectiveness (PROMOTE): study protocol for randomized controlled trial," *Trials*, 2015, 16:77, 14 pages.
Kloppenburg et al., "OARSI Clinical Trials Recommendations: Design and conduct of clinical trials for hand osteoarthritis," *Osteoarthritis and Cartilage*, 2015, 23:772-786.
Moher et al., "CONSORT 2010 Explanation and Elaboration: updated guidelines for reporting parallel group randomized trials," *Journal of Clinical Epidemiology*, 2010, 63:el-e37.
Neogi et al., "Sensitivity and sensitization in relation to pain severity in knee osteoarthritis: trait or state?" *Ann. Rhem. Dis.*, 2015, 74(4):682-688.
Ohtori et al., "Efficacy of Combination of Meloxicam and Pregabalin for Pain in Knee Osteoarthritis" *Yonsei Medical Journal*, 2013, 54(5):1253-1258.
Rahman et al., "Descending serotonergic facilitation and the antinociceptive effects of pegabalin in a rat model of osteoarthritic pain" *Molecular Pain*, 2009, 5(45), 16 pages.
Search Report issued in Corresponding UK IPO Patent Application No. GB 1617380.9, dated Jul. 13, 2017.
Sofat et al., "Pregabalin Is More Effective in Treating Hand Osteoarthritis Pain than Duloxetine or Placebo: A Double-Blind Randomized Controlled Trial" *Arthritis Rheumatol.*, 2016, 68(suppl 10): Abstract No. 3131, 3 pages.

(Continued)

*Primary Examiner* — Shobha Kantamneni
(74) *Attorney, Agent, or Firm* — Norton Rose Fulbright US LLP

(57) ABSTRACT

The present invention relates to the treatment of osteoarthritis with certain gamma-aminobutyric acid derivatives. Patients to be treated include those having elevated pain sensitivity. Specific therapies disclosed include those in which the gam-ma-aminobutyricacid derivative is administered as a single active agent rather than in combination with another active agent.

13 Claims, 7 Drawing Sheets

(56) References Cited

OTHER PUBLICATIONS

Suokas et al., "Quantitative sensory testing in painful osteoarthritis: a systematic review and meta-analysis" *Osteoarthritis and cartilage*, 2012, 20:1075-1085.

Thakur et al., "Characterisation of a Peripheral Neuropathic Component of the Rat Monoiodoacetate Model of Osteoarthritis" *PLoS ONE*, 2012, 7(3):e33730.

Wajed et al., "Pain Threshold testing Using Algometers is a Reliable measure of Pain in Hand Osteoarthritis and Correlates with Patient-Reported Pain Scores," *Rheumatology*, 2011, 50(suppl. 3):iii91(129).

Williams et al., "Efficacy of paracetamol for acute low-back pain: a double-blind, randomized controlled trial," *Lancet*, 2014, 384:1586-1596.

Wylde et al., "Test-retest reliability of Quantitative Sensory Testing in knee osteoarthritis and healthy participants" *Osteoarthritis and Cartilage*, 2011, 19:655-658.

\* cited by examiner

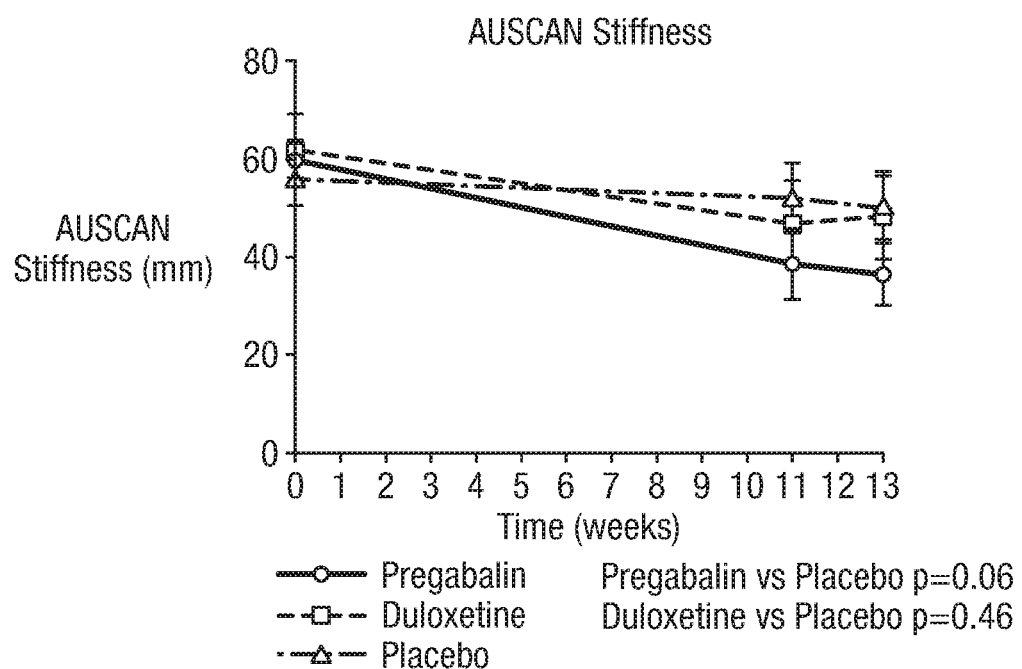

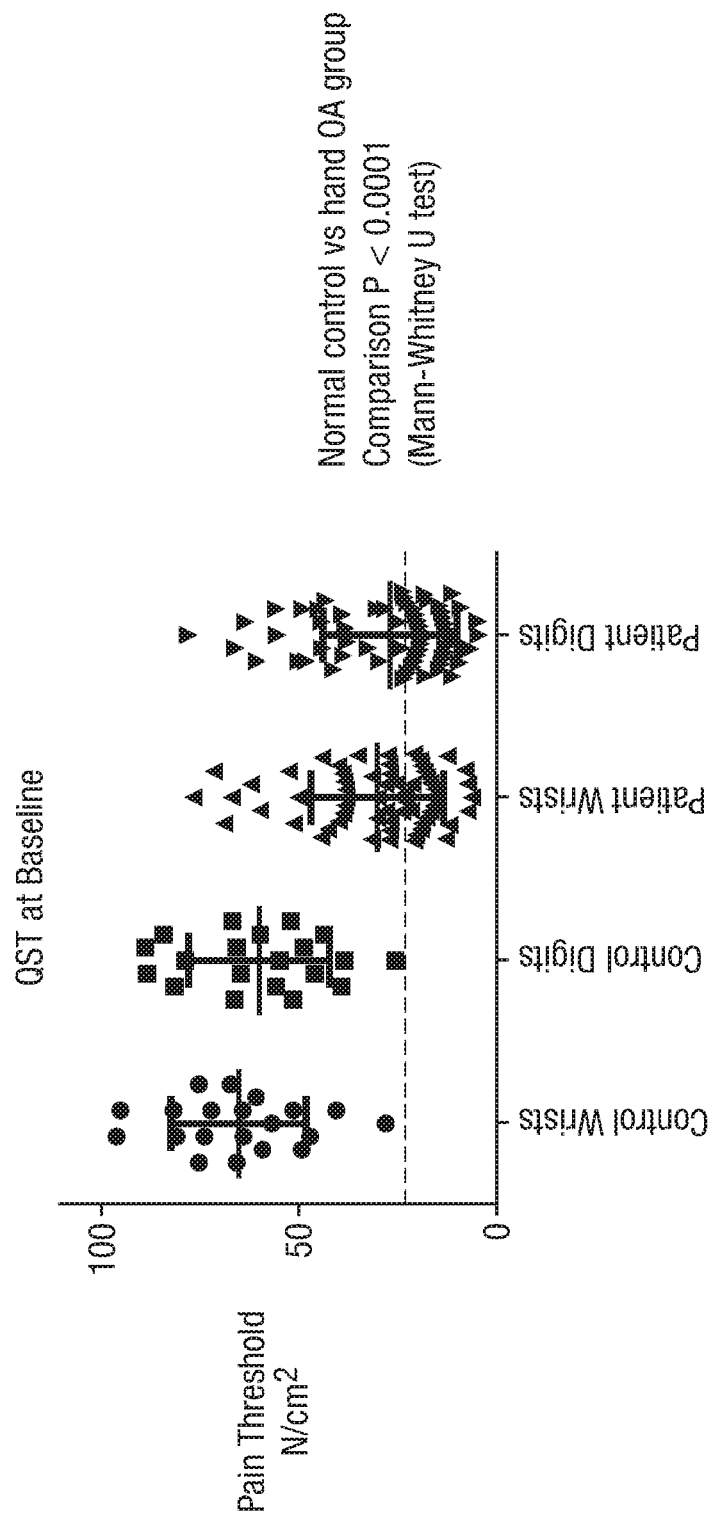

TREATMENT OF OSTEOARTHRITIS

CROSS-REFERENCE TO RELATED APPLICATION

This application is a national phase under 35 U.S.C. § 371 of International Application No. PCT/GB2017/053051, filed Oct. 9, 2017, which claims the benefit of priority to Great Britain Application No. 1617380.9, filed Oct. 13, 2016. The contents of each of the referenced applications are incorporated into the present application by reference.

FIELD OF THE INVENTION

The present invention relates to the treatment of osteoarthritis.

BACKGROUND TO THE INVENTION

Osteoarthritis (OA) is a type of joint disease associated with the breakdown of joint cartilage and the underlying bone. It is the most common form of arthritis and affects a substantial percentage of the adult population. For example, recent estimates from Arthritis Research UK suggest that around a third of people aged 45 years and over and up to around a half of people aged 75 years and over may be affected in the United Kingdom. OA can affect any joint, including the knee, hip, hand, wrist, foot and ankle.

Hand pain in particular is an increasingly prevalent condition among the ageing population, with OA a major cause. According to Arthritis Research UK, about 1 in 6 patients seeking treating for OA have hand or wrist OA.

Pain is the main symptom in OA leading patients to seek care. The associated reduction in function, inability to perform daily tasks due to pain and stiffness places a significant burden on patients and healthcare services. Many national and international guidelines for OA pain management include paracetamol, non-steroidal anti-inflammatory drugs (NSAIDs), and even opioids, but a large proportion of patients continue to suffer from pain despite using these interventions. Recent meta-analyses and new clinical trials have contradicted current guidelines for OA management, suggesting that paracetamol has poor efficacy in managing OA pain. Pain management in OA is therefore suboptimal for many and novel approaches are needed.

Centrally-acting analgesic drugs have been approved for the treatment of various pathological conditions having a pain component. For example, duloxetine is a serotonin and noradrenaline reuptake inhibitor (SNRI) that is approved for the treatment of diabetic neuropathy. It has also shown efficacy for pain outcomes in knee OA (Chappell et al., Pain 2009; 146(3): 253-60).

Another example of a centrally-acting analgesic drug is pregabalin, a derivative of the neurotransmitter gamma-aminobutyric acid (GABA). In WO 98/003167 pregabalin is disclosed and broadly asserted to be suitable for treating pain. Pregabalin is clinically approved for the treatment of neuropathic pain. One recent study also suggested that the combination of pregabalin and meloxicam (an NSAID used for treating OA) may be more effective for treating knee OA than either active agent alone (Ohtori et al., Yonsei Med J. 2013; 54(5): 1253-8).

However, no experimental evidence to date has indicated that pregabalin is suitable as a single active agent for treating OA, while no clinical data establishing any efficacy in treatment of hand OA has yet been published.

Recent concepts in the development of novel therapeutic agents for OA have included targeting specific aspects of disease. These have included potential therapeutics for structural changes in the joint including synovitis (Kingsbury et al., Trials 2015; 16: 77) and bone marrow lesions (Bruyere et al., Drugs and Aging. 2015; 32(3): 179-187).

However, such studies also highlight the unpredictable nature of the condition and its susceptibility for treatment. For example, a recent placebo controlled multi-centre trial concluded that the drug hydroxychloroquine, which has been used successfully for many years in the treatment of rheumatoid arthritis, did not reduce pain compared to placebo in patients suffering from primary hand OA (Basoki et al., Ann Rheum Dis 2015; 74: 188). A further illustration of this unpredictability in therapeutic outcome can be seen by contrasting the above-described finding of the efficacy of duloxetine for pain outcomes in knee OA, as against the finding, described in detail in the present working Examples, that this compound did not have a greater-than-placebo effect on pain outcomes in hand OA.

It would therefore be desirable to find new therapies for treating OA, particularly hand OA. Such new therapies should preferably be validated by clinical data evidencing their efficacy. It would also be desirable to target such new therapies to specific patients based on expected particularly efficacious outcomes.

SUMMARY OF THE INVENTION

It has now been found that a class of gamma-aminobutyric acid derivatives, including pregabalin, has significant efficacy in improving pain and joint function in patients suffering from hand OA. Pregabalin was, in particular, found to demonstrate significantly greater efficacy than an alternative centrally-acting analgesic drug, namely the well-known SNRI duloxetine which in previous reports has been suggested as a potential treatment for knee OA.

Furthermore, the observed efficacy was observed when the compound was administered as a single active agent and thus did not rely wholly or in part on co-administration with another pain management drug such as an NSAID.

Still further, treatment with the gamma-aminobutyric acid derivative may be particularly suitable for and/or achieve particularly beneficial results in patients demonstrating elevated pain sensitivity. Treatment with the gamma-aminobutyric acid derivative may comprise reducing this elevated pain sensitivity.

Additionally, treatment with the gamma-aminobutyric acid derivative may be particularly suitable for and/or achieve particularly beneficial results in patients having an abnormal insular cortex mI/Glx ratio. Furthermore, treatment with the gamma-aminobutyric acid derivative may be particularly suitable for and/or achieve particularly beneficial results in patients who have suffered from the OA for a particular duration. Patient groups characterised by particular combinations of two or more of elevated pain sensitivity, insular cortex mI/Glx ratio profile and disease duration may be especially well suited to efficacious treatment.

Specifically, the present invention provides, in a first aspect, a gamma-aminobutyric acid derivative for use in a method of treating hand osteoarthritis in a patient in need thereof, wherein said gamma-aminobutyric acid derivative is a compound of formula (I) or a pharmaceutically acceptable salt thereof

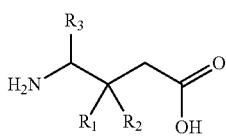

wherein
$R_1$ is a $C_{1-6}$ alkyl, phenyl, or $C_{3-6}$ cycloalkyl group;
$R_2$ is a hydrogen or methyl group; and
$R_3$ is a hydrogen, methyl, or carboxyl group.

The first aspect analogously provides use of a gamma-aminobutyric acid derivative in the manufacture of a medicament for use in a method of treating hand osteoarthritis in a patient in need thereof, wherein said gamma-aminobutyric acid derivative is a compound of formula (I) or a pharmaceutically acceptable salt thereof

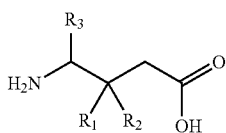

wherein
$R_1$ is a $C_{1-6}$ alkyl, phenyl, or $C_{3-6}$ cycloalkyl group;
$R_2$ is a hydrogen or methyl group; and
$R_3$ is a hydrogen, methyl, or carboxyl group.

The first aspect analogously provides a method of treating hand osteoarthritis in a patient in need thereof, wherein said method comprises administering to the patient a gamma-aminobutyric acid derivative which is a compound of formula (I) or a pharmaceutically acceptable salt thereof

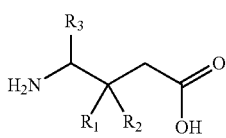

wherein
$R_1$ is a $C_{1-6}$ alkyl, phenyl, or $C_{3-6}$ cycloalkyl group;
$R_2$ is a hydrogen or methyl group; and
$R_3$ is a hydrogen, methyl, or carboxyl group.

The present invention also provides, in a second aspect, a gamma-aminobutyric acid derivative for use in a method of treating osteoarthritis in a patient in need thereof, wherein said patient has elevated pain sensitivity and wherein said gamma-aminobutyric acid derivative is a compound of formula (I) or a pharmaceutically acceptable salt thereof

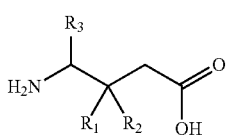

wherein
$R_1$ is a $C_{1-6}$ alkyl, phenyl, or $C_{3-6}$ cycloalkyl group;
$R_2$ is a hydrogen or methyl group; and
$R_3$ is a hydrogen, methyl, or carboxyl group.

The second aspect analogously provides use of a gamma-aminobutyric acid derivative in the manufacture of a medicament for use in a method of treating hand osteoarthritis in a patient in need thereof, wherein said patient has elevated pain sensitivity and wherein said gamma-aminobutyric acid derivative is a compound of formula (I) or a pharmaceutically acceptable salt thereof

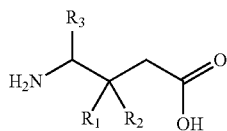

wherein
$R_1$ is a $C_{1-6}$ alkyl, phenyl, or $C_{3-6}$ cycloalkyl group;
$R_2$ is a hydrogen or methyl group; and
$R_3$ is a hydrogen, methyl, or carboxyl group.

The second aspect analogously provides a method of treating hand osteoarthritis in a patient in need thereof, wherein said patient has elevated pain sensitivity, and wherein said method comprises administering to the patient a gamma-aminobutyric acid derivative which is a compound of formula (I) or a pharmaceutically acceptable salt thereof

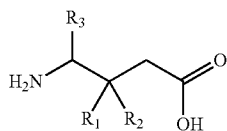

wherein
$R_1$ is a $C_{1-6}$ alkyl, phenyl, or $C_{3-6}$ cycloalkyl group;
$R_2$ is a hydrogen or methyl group; and
$R_3$ is a hydrogen, methyl, or carboxyl group.

In the second aspect the OA is preferably hand OA.

The present invention also provides, in a third aspect, a gamma-aminobutyric acid derivative for use in a method of treating osteoarthritis in a patient in need thereof, wherein said method comprises administering the gamma-aminobutyric acid derivative as a single active agent and wherein said gamma-aminobutyric acid derivative is a compound of formula (I) or a pharmaceutically acceptable salt thereof

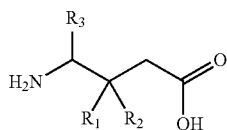

wherein
$R_1$ is a $C_{1-6}$ alkyl, phenyl, or $C_{3-6}$ cycloalkyl group;
$R_2$ is a hydrogen or methyl group; and
$R_3$ is a hydrogen, methyl, or carboxyl group.

The third aspect analogously provides use of a gamma-aminobutyric acid derivative in the manufacture of a medicament for use in a method of treating osteoarthritis in a patient in need thereof, wherein said method comprises administering the gamma-aminobutyric acid derivative as a single active agent and wherein said gamma-aminobutyric acid derivative is a compound of formula (I) or a pharmaceutically acceptable salt thereof

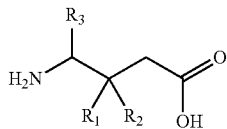

wherein
$R_1$ is a $C_{1-6}$ alkyl, phenyl, or $C_{3-6}$ cycloalkyl group;
$R_2$ is a hydrogen or methyl group; and
$R_3$ is a hydrogen, methyl, or carboxyl group.

The third aspect analogously provides a method of treating osteoarthritis in a patient in need thereof, wherein said method comprises administering to the patient, as a single active agent, a gamma-aminobutyric acid derivative which is a compound of formula (I) or a pharmaceutically acceptable salt thereof

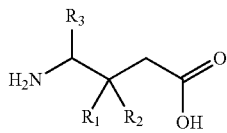

wherein
$R_1$ is a $C_{1-6}$ alkyl, phenyl, or $C_{3-6}$ cycloalkyl group;
$R_2$ is a hydrogen or methyl group; and
$R_3$ is a hydrogen, methyl, or carboxyl group.

In the third aspect the OA is preferably hand OA.

The present invention also provides, in a fourth aspect, a gamma-aminobutyric acid derivative for use in a method of treating osteoarthritis in a patient in need thereof, wherein said gamma-aminobutyric acid derivative is a compound of formula (I) or a pharmaceutically acceptable salt thereof

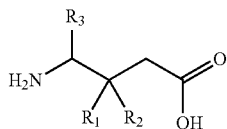

wherein
$R_1$ is a $C_{1-6}$ alkyl, phenyl, or $C_{3-6}$ cycloalkyl group;
$R_2$ is a hydrogen or methyl group; and
$R_3$ is a hydrogen, methyl, or carboxyl group;
with the proviso that said method does not comprise co-administering the gamma-aminobutyric acid derivative with meloxicam.

The fourth aspect analogously provides use of a gamma-aminobutyric acid derivative in the manufacture of a medicament for use in a method of treating osteoarthritis in a patient in need thereof, wherein said method comprises administering the gamma-aminobutyric acid derivative and wherein said gamma-aminobutyric acid derivative is a compound of formula (I) or a pharmaceutically acceptable salt thereof

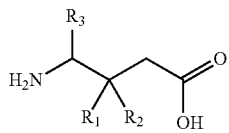

wherein
$R_1$ is a $C_{1-6}$ alkyl, phenyl, or $C_{3-6}$ cycloalkyl group;
$R_2$ is a hydrogen or methyl group; and
$R_3$ is a hydrogen, methyl, or carboxyl group;
with the proviso that said method does not comprise co-administering the gamma-aminobutyric acid derivative with meloxicam.

The fourth aspect analogously provides a method of treating osteoarthritis in a patient in need thereof, wherein said method comprises administering to the patient a gamma-aminobutyric acid derivative which is a compound of formula (I) or a pharmaceutically acceptable salt thereof

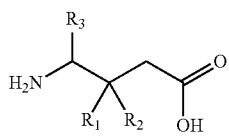

wherein
$R_1$ is a $C_{1-6}$ alkyl, phenyl, or $C_{3-6}$ cycloalkyl group;
$R_2$ is a hydrogen or methyl group; and
$R_3$ is a hydrogen, methyl, or carboxyl group;
with the proviso that said method does not comprise co-administering the gamma-aminobutyric acid derivative with meloxicam.

In the fourth aspect the OA preferably comprises one or more of hand OA, knee OA and hip OA and more preferably comprises hand OA (optionally with at least one or both of knee OA and hip OA). In the fourth aspect the method preferably does not comprise co-administering the gamma-aminobutyric acid derivative with an NSAID.

Embodiments of the first, second, third and fourth aspects include the following:
(i) the gamma-aminobutyric acid derivative is pregabalin;
(ii) the method comprises administering the gamma-aminobutyric acid derivative as a single active agent;
(iii) the patient has elevated pain sensitivity, and optionally the method comprises reducing said elevated pain sensitivity;
(iv) the method comprises one, two or three of: reducing joint pain in the patient; improving joint function in the patient; and reducing joint stiffness in the patient;
(v) the patient has an elevated insular cortex mI/Glx ratio;
(vi) the patient has a depressed insular cortex mI/Glx ratio;
(vii) the patient is greater than or equal to 65 years old; and
(viii) the patient is less than 65 years old.

For the avoidance of doubt, these embodiments can be combined unless context clearly dictates otherwise. Furthermore, these first, second and third aspects, and these embodiments thereof can be combined with other optional features of the present invention as disclosed elsewhere herein unless context clearly dictates otherwise.

BRIEF DESCRIPTION OF THE FIGURES

FIG. 4 shows data for QST in PPT (N/cm$^2$) from the trial discussed in Example 1, demonstrating pain thresholds globally in the wrist and finger joints in hand OA participants compared with normal age- and sex-matched controls.

DETAILED DESCRIPTION

The Gamma-Aminobutyric Acid Derivative

Figure 1:
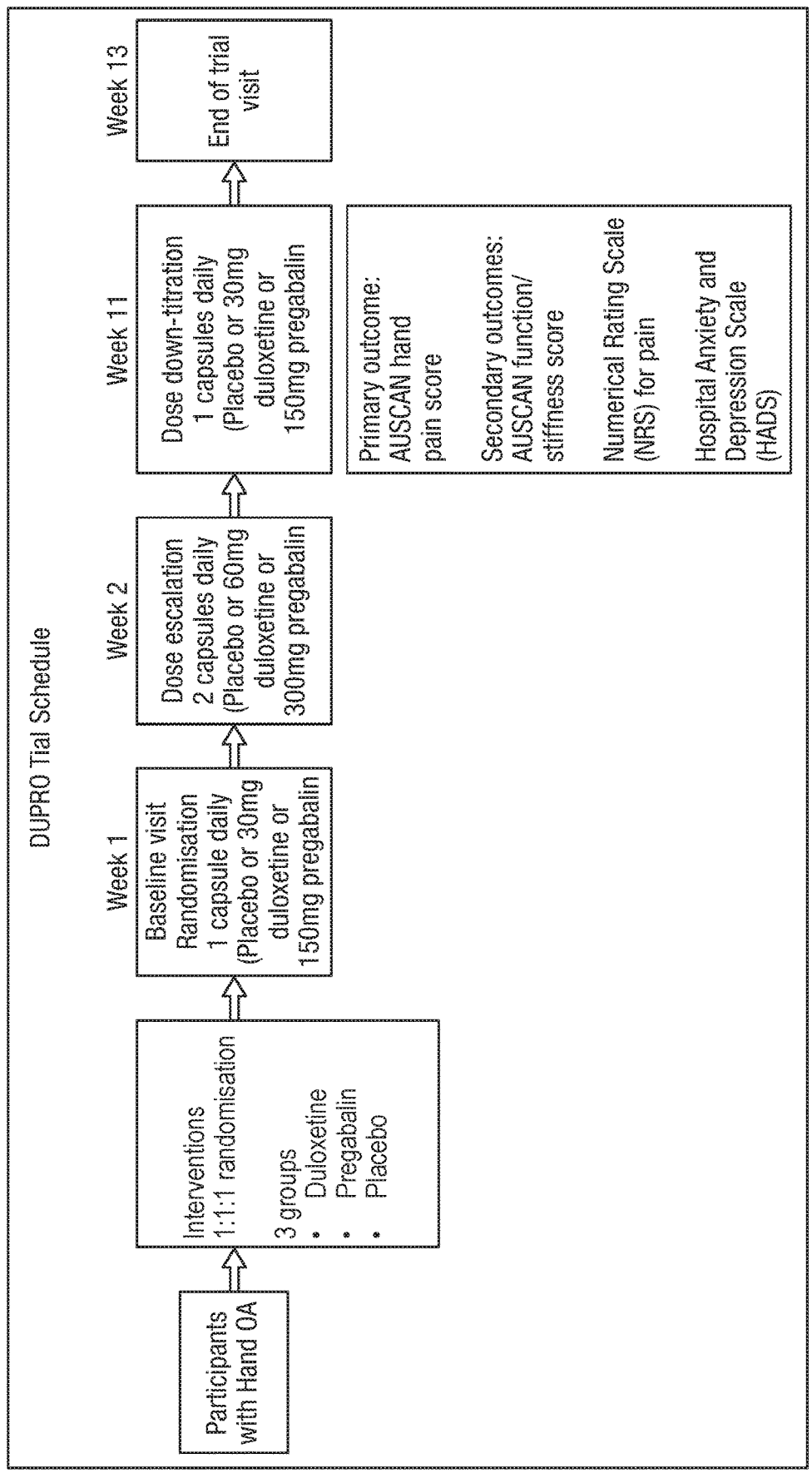
FIG. 1 shows schematically the trial schedule discussed in Example 1.

The gamma-aminobutyric acid derivative is a compound of formula (I) or a pharmaceutically acceptable salt thereof

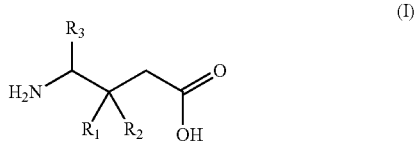

(I)

wherein
$R_1$ is a $C_{1-6}$ alkyl, phenyl, or $C_{3-6}$ cycloalkyl group;
$R_2$ is a hydrogen or methyl group; and
$R_3$ is a hydrogen, methyl, or carboxyl group.

An alkyl group may be a straight-chain or branched-chain alkyl group. $C_{1-6}$ alkyl includes methyl, ethyl, propyl, butyl, pentyl and hexyl. $C_{3-6}$ cycloalkyl includes cyclopropyl, cyclobutyl, cyclopentyl, and cyclohexyl.

Preferably $R_1$ is a $C_{1-6}$ alkyl group, more preferably a —$(CH_2)_{0-2}$-$iC_4H_9$ group and most preferably an -$iC_4H_9$ group (i.e., an isobutyl group). Preferably $R_2$ is hydrogen. Preferably $R_3$ is hydrogen. A particularly preferred compound of formula (I) is one in which $R_1$ is an -$iC_4H_9$ group and $R_2$ and $R_3$ are both hydrogen. A particularly preferred gamma-aminobutyric acid derivative is the compound of formula (I) in which $R_1$ is an -$iC_4H_9$ group and $R_2$ and $R_3$ are both hydrogen.

Compounds of formula (I) can contain one or several asymmetric carbon atoms. The invention includes the individual diastereomers or enantiomers, and the mixtures thereof. The individual diastereomers or enantiomers may be prepared or isolated by methods already well-known in the art.

Most preferably the compound of formula (I) is pregabalin, i.e. (3S)-3-(aminomethyl)-5-methylhexanoic acid. For example, the gamma-aminobutyric acid derivative is pregabalin.

The compound of formula (I) may form pharmaceutically acceptable salts with both acids or bases, which both may be organic or inorganic. For example, an acid addition salt of the basic compound can be prepared either by dissolving the free base in aqueous or aqueous alcohol solution or other suitable solvents containing the appropriate acid and isolating the salt by evaporating the solution. Non-limiting examples of pharmaceutically acceptable salts include hydrochloride, hydrobromide, hydrosulfate, mandelate, besylate and tosylate as well as sodium, potassium, and magnesium salts.

Synthetic methods for preparing compounds of formula (I) and pharmaceutically salts thereof are well known in the art. For example, suitable methods are described in WO 98/003167, the contents of which are herein incorporated by reference in their entirety.

Osteoarthritis

Where the present invention involves a method of treating osteoarthritis (OA), the OA may include one or more of knee OA, hip OA, hand OA, wrist OA, foot OA and ankle OA. Preferably the OA comprises hand OA.

For the avoidance of doubt, references herein to hand OA, and associated methods of treating hand OA, do not exclude the possibility that the patient also suffers from OA of one or more other joints. For example, a patient suffering from hand OA may also suffer from one or more of knee OA, hip OA, wrist OA, foot OA and ankle OA, such as one or both of hip OA and knee OA.

OA consists of different phenotypes. In primary OA, there is little or no other underlying disease contributing to OA pathology. The typical features include cartilage degradation, osteophyte formation with bone cysts and sclerosis. Such OA can affect the hands, knees, hips and spine most commonly.

Patients with secondary OA e.g., post-traumatic arthritis, calcium pyrophosphate deposition disease, hemochromatosis, or patients with exacerbating factors related to primary OA e.g., inflammatory or genetic factor, are also recognised. "At risk" groups for genetically predisposed OA include people with type II collagen mutations e.g. Stickler syndrome and Marshall syndrome. Patients with such genetic defects often develop early and aggressive OA.

The OA may be primary OA or secondary OA. Specifically, the patient may have either primary or secondary OA. In one embodiment, the patient has primary OA. In an alternative embodiment, the patient has secondary OA.

Administration as a Single Active Agent or in the Absence, or Presence, of Certain Active Agents In some embodiments of the present invention the gamma-aminobutyric acid derivative is administered as a single active agent. One aspect of the present invention is the surprising finding that a gamma-aminobutyric acid derivative such as pregabalin is clinically effective in treating OA without being co-administered with an NSAID—the use of which in managing OA is already well established.

Administration "as a single active agent" means that, during the period of treatment with the gamma-aminobutyric acid derivative, no other pharmaceutically active compound is administered for treating the OA. Other pharmaceutically active compound for treating OA include paracetamol, non-steroidal anti-inflammatory drugs (NSAIDs), opioids and centrally-acting analgesic drugs other than the gamma-aminobutyric acid derivative.

In general, administration of the gamma-aminobutyric acid derivative as a single active agent does not excludes co-administration of the gamma-aminobutyric acid derivative with substances that are being administered for therapeutic purposes other than the treatment of the OA. For example, in a patient suffering from OA and another distinct, for example medically unrelated, condition, administration of the gamma-aminobutyric acid derivative as a single active agent does not preclude the administration, during the period of treatment with the gamma-aminobutyric acid derivative, of one or more active agents for treating the condition distinct from OA.

In the present invention, the gamma-aminobutyric acid derivative is preferably not co-administered with an NSAID, for example it is not co-administered with meloxicam.

Optionally the gamma-aminobutyric acid derivative is not co-administered with an opioid. Optionally the gamma-aminobutyric acid derivative is not co-administered with another centrally-acting analgesic drug, for example duloxetine. Optionally the gamma-aminobutyric acid derivative is not co-administered with paracetamol.

Alternatively, however, in aspects where the gamma-aminobutyric acid derivative is not specified as being administered as a single active agent (such as the first and second aspects as defined elsewhere herein), it may be co-administered with one or more other active agents used in the treatment of OA, for example paracetamol, an NSAID an opioid or another centrally-acting analgesic drug. In one such embodiment, paracetamol is co-administered as a "rescue medication" in the event that the patient's symptoms (for example, intensity of pain or lack of joint function) are considered sufficiently severe, either by the patient or by a responsible medical practitioner.

The gamma-aminobutyric acid derivative may also be co-administered with an NSAID, i.e., the relevant method of treatment may comprise co-administering the gamma-aminobutyric acid derivative with an NSAID. The invention thus embraces a combination product comprising the gamma-aminobutyric acid derivative and an NSAID for use in the relevant method of treatment; the combination product may comprise the gamma-aminobutyric acid derivative and the NSAID in a single pharmaceutical composition or separate pharmaceutical compositions. Such a combination therapy may give rise to synergistic benefits, for example the therapeutic efficacy achieved may be greater than that expected, e.g. on an additive basis, from the efficacies associated with the respective monotherapies.

Co-administration embraces combined, concurrent and sequential administration of the gamma-aminobutyric acid derivative and the one or more other active agents.

Effects of Treatment

Another aspect of the present invention is the finding that a gamma-aminobutyric acid derivative such as pregabalin achieves substantial beneficial effects of a specific nature in the treatment of OA, which effects surprisingly are significantly more pronounced than in treatment with the comparator compound duloxetine. Like pregabalin, duloxetine is a centrally-acting analgesic compound. Unlike pregabalin, however, duloxetine has previously been tested as a single active agent in a clinical trial for OA, specifically wherein it was found to show efficacy for pain outcomes in knee OA (Chappell et al., Pain 2009; 146(3): 253-60). The significantly enhanced efficacy of pregabalin compared with duloxetine in treating hand OA is unexpected in the light of this previous work.

Beneficial effects of treatment with the gamma-aminobutyric acid derivative include one or more of
(i) reducing joint pain in the patient;
(ii) improving joint function in the patient; and
(iii) reducing joint stiffness in the patient.

Where the OA treated is hand OA, the relevant joints in the joint pain, joint function and joint stiffness are of course the joints in the hand. Thus, the beneficial effects conferred correspond to one or more of reduced hand pain, improved hand function and reduced hand stiffness.

Preferably two or more, and most preferably all of the above pain, function and stiffness are ameliorated upon treatment with the gamma-aminobutyric acid derivative.

Beneficial effects can be assessed using routine techniques that are well known in the art. For example, in the case of treatment of hand OA, effects in reducing hand pain, improving hand function and reducing hand stiffness can in one non-limiting embodiment be assessed according to the Australian and Canadian Hand Osteoarthritis Index (AUSCAN) rating scale 3.1. More exemplary details are provided in Example 1.

Other beneficial effects conferred by treatment according to the present invention may include a reduced pain measured in accordance with the Numerical Rating Scale (NRS) pain rating (0-10) as well as any of numerous other widely utilised pain assessment methodologies, including but not limited to those discussed in the present Examples.

A still further beneficial effect that may be conferred by treatment according to the present invention is reduction in pain sensitivity, particularly in patients having an elevated pain sensitivity prior to treatment with the gamma-aminobutyric acid derivative. Further details of methods for assessing pain sensitivity and changes therein are provided elsewhere herein.

Patient Groups

The patient is typically a human patient.

A further aspect of the present invention is the finding that the gamma-aminobutyric acid derivative may be particularly efficaciously targeted to specific patients. By "particularly efficaciously targeted" is meant that administration of the gamma-aminobutyric acid derivative to the specific patients achieves beneficial effects (e.g. such as those specific effects outlined elsewhere herein) of greater magnitude than does administration to other patients suffering from OA.

Pain Sensitivity

One group of patients who may benefit particularly from treatment in accordance with the present invention are patients having elevated pain sensitivity.

Pain sensitivity refers to a patient's subjective assessment of the magnitude of pain whose actual magnitude is fixed. Pain sensitivity can readily be measured by those skilled in the art, for example by utilising any of many well known and scientifically accepted techniques for measuring pain threshold.

Preferably, the elevated pain sensitivity corresponds to elevated pain sensitivity in the vicinity of the joint or joints associated with the OA to be treated. For example, where the treatment comprises treatment of hand OA, the patient may have elevated pain sensitivity in the hand.

One example of a suitable method for measuring pain sensitivity comprises testing the patient's pain pressure threshold (PPT), such as by using an algometer. One exemplary embodiment in the context of hand OA involves recording pain pressure thresholds with an algometer in some or all of the 30 joints of the hands and wrists (e.g. all 30 joints); such an approach is described in more detail in Example 1.

An elevated pain sensitivity means that the patient is more sensitive to pain, for example has a lower pain threshold, such as a lower pain pressure threshold (PPT), than a control level. The difference between the patient's pain sensitivity and the control value is typically one that is significant when measured in accordance with an appropriate statistical technique. Methods for determining elevated pain sensitivity when pain sensitivity is measured in a particular manner are routine and easily be carried out by those skilled in the art; they are also exemplified in the Examples.

In one embodiment, the control level corresponds to the average pain sensitivity of subjects other than the patient. The subjects other than the patient may be age-matched to the patient and may also be screened to remove other potentially confounding factors. The subjects other than the patient may have the OA, e.g. they may also have hand OA (thus meaning that the elevated pain sensitivity of the patient indicates elevated pain sensitivity relative to a patient population, as a whole, having the OA). Alternatively the subjects other than the patient may not have the OA (thus meaning that the elevated pain sensitivity of the patient indicates elevated pain sensitivity relative to subjects not having the OA). In a still further alternative the subjects other than the patient comprise a mixture of those having the OA and not having the OA.

In another embodiment, the control level instead corresponds to the pain sensitivity of the patient himself or herself, but measured at an earlier time. Thus, the patient is one whose pain sensitivity has increased over time. Detection of an increase in pain sensitivity may be indicative that the patient is particularly susceptible to treatment in accordance with the present invention. In one non-limiting example, the elevated pain sensitivity corresponds to an increase in pain sensitivity over a period of up to five years (for example, 3 to 5 years). In another non-limiting example, the elevated pain sensitivity corresponds to an increase in pain sensitivity over a period of 6 to 12 months, or 3 to 6 months, or 1 to 3 months.

Treatment in accordance with the present invention may lead to a reduction in the patient's pain sensitivity. Reduction in pain sensitivity can of course be determined by comparing pain sensitivity, measured according a chosen test, prior to the commencement of treatment with pain sensitivity, measured according to the same test, during and/or after the culmination of treatment.

Abnormal mI/Glx Ratio

Another group of patients who may benefit particularly from treatment in accordance with the present invention comprises patients having abnormal insular cortex mI/Glx ratio. mI refers to the amount of myo-Inositol, Glx refers to the total amount of glutamic acid (Glu) and glutamine (Gln).

An exemplary method for determining the amounts of insular cortex mI and Glx is set out in Example 2. Other suitable methods can of course also be used.

It has been found that abnormal insular cortex mI/Glx ratio in a subject correlates with perceived pain in OA patients, which itself correlates with sensitisation mechanisms suggestive of susceptibility to treatment with a gamma-aminobutyric acid derivative such as pregabalin. Without wishing to be bound by theory, determination of an abnormal insular cortex mI/Glx ratio, as further specified herein, in a patient suffering OA may thus provide a motivation for treatment with a gamma-aminobutyric acid derivative such as pregabalin.

An abnormal level insular cortex mI/Glx ratio means a significant change in insular cortex mI/Glx ratio relative to a control level. A significant change will typically mean a change which is significant when measured in accordance with an appropriate statistical technique. Appropriate techniques are well-known in the art and are exemplified in the Examples.

In one embodiment, the control level corresponds to the average insular cortex mI/Glx ratio of subjects other than the patient. The subjects other than the patient may be age-matched to the patient and may be further screened to remove other potentially confounding factors. The subjects other than the patient may have the OA, e.g. they may also have hand OA. Alternatively the subjects other than the patient may not have the OA. In a still further alternative the subjects other than the patient comprise a mixture of those having the OA and not having the OA.

In another embodiment, the control level instead corresponds to the insular cortex mI/Glx ratio of the patient himself or herself, but measured at an earlier time. Thus, the patient is one in which the insular cortex mI/Glx ratio has changed over time. In one non-limiting example, the insular cortex mI/Glx ratio corresponds to a change in insular cortex mI/Glx ratio over a period of up to five years (for example, 3 to 5 years). In another non-limiting example, the elevated pain sensitivity corresponds a change in insular cortex mI/Glx ratio over a period of 6 to 12 months, or 3 to 6 months, or 1 to 3 months.

Without wishing to be bound by theory, it is believed that the abnormal level insular cortex mI/Glx ratio may also be correlated with the age of the patient. For example, it is believed (including in the light of the results presented in the accompanying Examples) that the origins of the pain underlying the OA, as manifesting themselves inter alia in the observed abnormal insular cortex mI/Glx ratio, may change with age. For example, a sensitisation component may become more prominent with increasing age. The component becoming more prevalent age may be particularly susceptible to treatment with the gamma-aminobutyric acid derivative.

Thus, for example, an elevated insular cortex mI/Glx ratio may be an abnormal insular cortex mI/Glx ratio indicative of particular susceptibility to treatment according to the present invention in an older patient, whereas a depressed insular cortex mI/Glx ratio may be an abnormal insular cortex mI/Glx ratio indicative of particular susceptibility to treatment according to the present invention in a younger patient. By an "older patient" is meant that the patient may be greater than or equal to, for example, 50 years old or preferably 55 years old, more preferably 60 years old and more preferably still 65 years old. By a "younger patient" is meant that the patient may be less than, for example, 75 years old or preferably 70 years old and more preferably 65 years old.

In one embodiment, the patient has an elevated insular cortex mI/Glx ratio. Preferably the said patient is greater than or equal to 65 years old.

In another embodiment, the patient has a depressed insular cortex mI/Glx ratio. Preferably the said patient is less than 65 years old.

Duration of Disease

A further group of patients who may benefit particularly from treatment in accordance with the present invention are patients who have been suffering from the OA for a particularly long period of time. Without wishing to be bound by theory, treatment by conventional means (e.g. using paracetamol, NSAIDs, opioids and other strategies) may be less effective or even entirely ineffective in such patients, meaning that treatment with the gamma-aminobutyric acid derivative may be associated with particularly beneficial effects in comparison. Alternatively or additionally, the origins of the pain underlying the OA may change with the duration of the disease. For example, a sensitisation component may become more prominent with increasing duration. The component becoming more prevalent with duration may be particularly susceptible to treatment with the gamma-aminobutyric acid derivative.

Accordingly, treatment with the gamma-aminobutyric acid derivative may be particularly beneficial for patients who have suffered from the OA for at least 1 year, preferably at least 2 years, more preferably at least 5 years and most preferably at least 10 years. For example, the treatment with the gamma-aminobutyric acid derivative may be particularly beneficial for patients who were first diagnosed with the OA at least one year, preferably at least 2 years, more preferably at least 5 years and most preferably at least 10 years previously.

Patients for Whom Existing Treatments are not Practicable

A still further group of patients who may benefit particularly from treatment in accordance with the present invention are patients for whom treatment with paracetamol, NSAIDs and/or opiates have lost analgesic effect or are associated with unacceptable side effects. In particular, the patient may be one for whom treatment with one or more of (a) paracetamol, (b) NSAIDs and (c) opiates, for example all of (a) to (c), is not therapeutically effective, wherein therapeutically effective means at least one clinically significant beneficial effect without a clinically prohibitive side effect profile. Medical practitioners are, of course, readily capable, as part of their routine day-to-day work, of determining when treatment with a particular drug compound is not (or is no longer) therapeutically effective in this context. The gamma-aminobutyric acid derivative provides an alternative treatment strategy, having a different mechanistic basis, for patients for whom these conventional treatments are not or are no longer available.

Pharmaceutical Compositions

The gamma-aminobutyric acid derivative may be administered as a pharmaceutical composition by any suitable route. For example, administration may be oral (as syrups, tablets, capsules, lozenges, controlled-release preparations, fast-dissolving preparations, etc), topical (as creams, ointments, lotions, nasal sprays or aerosols, etc), by injection (subcutaneous, intradermal, intramuscular, intravenous, etc), or by inhalation (as a dry powder, a solution, a dispersion, etc). In an exemplary embodiment the gamma-aminobutyric acid derivative is formulated for oral delivery, such as in solid form (e.g. as a tablet or capsule). For example, compositions formulated for oral delivery identical to, or based on, commercially available forms of pregabalin for use in treating currently approved indications may be used.

Pharmaceutical compositions comprising the gamma-aminobutyric acid derivative may be prepared any suitable method known to those of skill in the art. The pharmaceutical compositions typically comprises one or more pharmaceutically acceptable excipients or diluents.

The one or more pharmaceutically acceptable excipients or diluents may be any suitable excipients or diluents. For example, a pharmaceutical composition which is a solid oral form may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tableting, sugar coating, or film coating processes.

A pharmaceutical composition which is a liquid dispersion for oral administration may be a syrup, emulsion and suspension. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

To the extent that the underlying method does not involve administration of the gamma-aminobutyric acid derivative as a sole active agent (as discussed elsewhere herein), pharmaceutical compositions of the invention may comprise additional active ingredients, such as an additional therapeutic or prophylactic agent intended, for example, for the treatment of the same condition or a different one, or for other purposes such as amelioration of side effects.

Dosages

A suitable dosage of the gamma-aminobutyric acid derivative may be determined by a skilled medical practitioner. In the methods described herein, the gamma-aminobutyric acid derivative is administered to the patient in an effective amount. Effective in this context means that a significant beneficial effect is experienced by the patient, for example one or more of the effects discussed elsewhere herein. The effective amount is thus a therapeutically effective amount.

The dosage of the gamma-aminobutyric acid derivative may typically range from about 1 to about 1000 mg, preferably about 1 to about 600 mg per day, more preferably about 50 to about 500 mg per day, for example about 100 to 400 mg per day. The dosage of the gamma-aminobutyric acid derivative may typically range from about 0.01 to about 15 mg/kg per day, preferably about 0.01 to about 10 mg/kg per day, more preferably about 0.5 to about 7.5 mg/kg per day, for example about 1.5 to 6 mg/kg per day. The dosages, however, may be varied depending upon the requirement with a patient, the severity of the condition being treated, and the specific compound being employed.

The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Dosage regimens may be adjusted to provide the optimum desired response. For example, a single dose may be administered, several divided doses may be administered over time or the dose may be proportionally reduced or increased as indicated by the exigencies of the therapeutic situation. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Administration may be in single or multiple doses. Multiple doses may be administered via the same or different routes and to the same or different locations. Alternatively, doses can be via a sustained release formulation, in which case less frequent administration is required. Dosage and frequency may vary depending on the half-life of the drugs in the patient and the duration of treatment desired.

Determination of the proper dosage for particular situations is within the skill of the art.

Example 1

A trial was conducted to test the analgesic effects of centrally-acting analgesics duloxetine and pregabalin in painful hand OA refractory to conventional analgesics. The safety and tolerability of these agents used in this context was secondarily explored, and pain sensitisation measures were assessed.

Methods

Trial Design and Participants

Ethical approval was provided by the UK Health Research Authority approval number 12/LO/0047. Enrolment of hand OA participants was conducted through rheumatology clinics and general practices throughout the South London region as part of the NIHR Clinical Research Network (CRN). Non-OA controls for pain measures were recruited through poster advertisements.

Inclusion criteria: Participants were eligible for screening if they were aged 40-75 years, had hand OA diagnosed by ACR criteria (Altman et al., Arthritis and Rheumatism 1990; 33(11): 1601-10) confirmed by a rheumatologist and experiencing pain of at least 5 or above on a numerical rating scale (NRS) of 0-10. Criteria also stated that participants experience sustained pain despite treatment with usual care including paracetamol and/or NSAIDs as per UK NICE guidelines for OA. All participants underwent baseline hand radiography to confirm radiographic evidence of OA. The radiographic findings were used to confirm radiographic evidence of OA from ACR criteria of at least 3 joints affected, with a Kellgren-Lawrence grade (Kellgren et al., Ann Rheum Dis 1957; 16(4): 494-502) of 2 or above in at least 3 affected joints. Radiographic scoring was performed after a training session independently by 2 researchers. Participants were informed that they would undergo pain testing including tests for sensitisation as part of the study.

Exclusion Criteria

Exclusion included other rheumatological diagnoses e.g. (rheumatoid arthritis, psoriatic arthritis, systemic lupus erythematosus (SLE), fibromyalgia), current or planned pregnancy, contraindications to duloxetine or pregabalin, history of clinically-diagnosed depression or anxiety disorder, recent surgery or previous use of duloxetine or pregabalin due to potential bias or confounding effects.

Randomisation and Procedures

Study drugs were supplied by Sharp Clinical Services (formerly Bilcare GCS (Europe), Powys, UK), which over-encapsulated pregabalin 150 mg tablets or duloxetine 30 mg tablets and produced visually identical placebo capsules. The random allocation sequence, with a block size of nine, was generated by the manufacturer and implemented through sequentially numbered containers. Neither participants nor investigators were aware of treatment assignment until after data lock. Emergency code breaks were administered independently of the trial investigators by staff in the St George's University Hospitals NHS Foundation Trust Clinical Trials Pharmacy.

The trial schedule is summarised in FIG. 1. Participants were randomly assigned to duloxetine 30 mg, pregabalin 150 mg or matched placebo, starting at one capsule for one week, incrementing to one capsule twice daily from week 2 to week 11 then reducing down to one capsule in the final week 12 to ensure minimal withdrawal side-effects. Participants were issued with a diary card with their medication to be completed for VAS pain rating on a daily basis. Randomisation was conducted 1:1:1 for duloxetine, pregabalin and placebo. The protocol recommended that participants should record use of rescue medication (paracetamol up to 4 g daily) in their diary card. Open-label oral pregabalin or duloxetine was prohibited. All other care was at the discretion of the treating physicians.

Objective pain measures at baseline and after 13 weeks included Quantitative Sensory Testing (QST) and brain Magnetic Resonance Imaging (MRI) (reported separately in Example 2 below).

Outcomes

The primary end point was the Australian and Canadian Hand Osteoarthritis Index (AUSCAN) rating scale 3.1 with sub-scales for pain, which is a validated measure of hand pain, stiffness and function in clinical trials of hand OA (Bellamy et al., Arthritis Care Res (Hoboken) 2015; 67(7): 972-80). Based on IMMPACT guidelines for pain trials (Dworkin et al., Pain 2005; 113: 9-19), primary end-point data for the AUSCAN pain sub-scale was collected. The primary endpoint was change in AUSCAN pain between baseline and 13 weeks. Patient-reported symptoms were recorded in three domains and participants asked to record their scores based on symptoms 'in the last 48 hours'. Pain reporting consists of 5 questions, rated at 0-100 mm each, for pain in the hands at rest, gripping objects, turning and squeezing objects, scoring out of a total of 500.

For secondary outcome data, the AUSCAN stiffness and function scales were recorded; there was one question for stiffness symptoms (0-100 mm) and 3 questions testing function (0-100 mm each). Additional secondary outcomes included the Numerical Rating Scale (NRS) pain rating 0-10, the Hospital Anxiety and Depression Scale (HADS) (Bjelland et al., Journal of Psychosomatic Research. 2002; 52(2): 69-77) and pain sensitisation measures in the three treatment groups at baseline and at week 13. Operational definitions for all end points, including time points for comparisons, were specified prospectively in the trial protocol.

Quantitative sensory testing was used to obtain objective measures of peripheral pain sensitisation as described in Wajed et al., Rheumatology 2011; 50 (suppl 3): iii91(129). Briefly, pain pressure thresholds (PPT) were recorded with a hand held algometer (Wagner instruments, USA) in all 30 joints of the hands and wrists and the mean of three readings recorded in kilopascals (kPa). All readings were obtained after the research team received a training session (NS and AH). Comparisons were made between control non-OA participants and the hand OA group.

All primary data were double entered and checked for consistency. Secondary data were checked after data entry.

Statistical Analysis

The sample size was based on the OARSI recommendations for RCTs on hand OA (Kloppenburg et al., Osteoarthritis Cartilage 2015; 23(5): 772-86). For AUSCAN pain scores, the aim was to detect a mean difference of 80 between baseline and treatment after 13 weeks using the AUSCAN pain score as the primary outcome measure with a sigma of 90. With 16 participants in each group, 80% power with a 0.05 significance level is achieved. This meant a recruitment of up to 22 participants per treatment group, allowing for a dropout rate of 25%, giving a total intervention study number of 65 participants to achieve desired statistical power. The AUSCAN pain, stiffness and function outcomes are presented as means and 95% confidence intervals. Analysed between group were comparisons by the Mann Whitney U test. Baseline characteristics in each group are shown by mean values and standard deviation. ANOVA comparisons between duloxetine, pregabalin and placebo groups was made with significance at p<0.05 used to compare any significant differences in the pregabalin, duloxetine or placebo groups for age, body mass index, mean baseline AUSCAN pain score, mean baseline numerical rating scale (NRS), mean baseline Hospital Anxiety and Depression Scale (HADS) and mean duration of diagnosis. IBM SPSS Statistics 21.0 was used for all analyses and graphs were plotted using Graphpad Prism version 6.

Role of the Funding Source

The trial was an investigator-initiated trial funded by the UK NIHR Clinical Research Network and The Rosetrees' Trust grant code CM11-F1. The funders of the study had no role in the study design, data collection, data analysis, data interpretation, or writing of the report.

Results

Characteristics of Patients and Treatment of Hand OA

Figure 2:
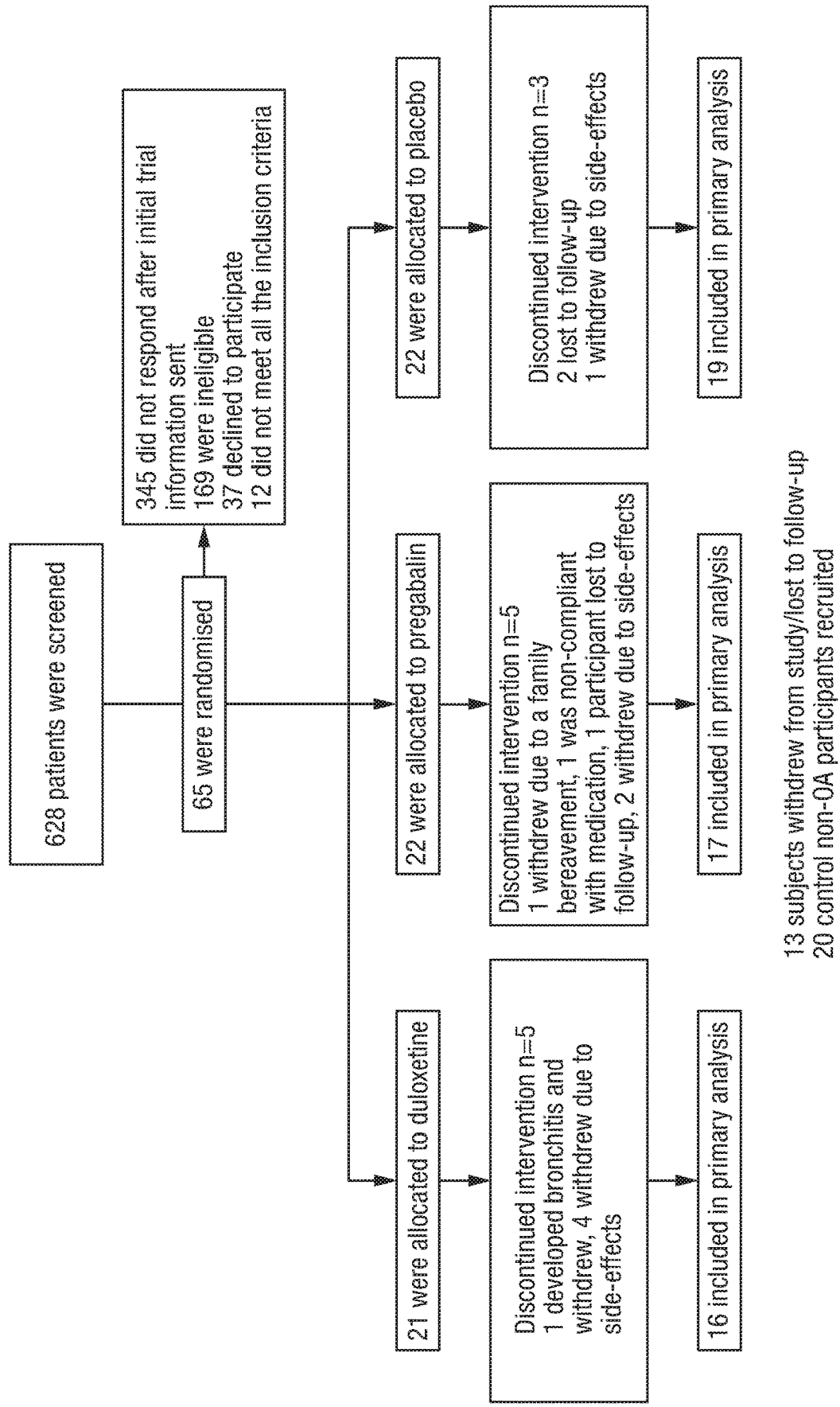
FIG. 2 shows a CONSORT flow diagram of the trial discussed in Example 1.
Figure 3A:
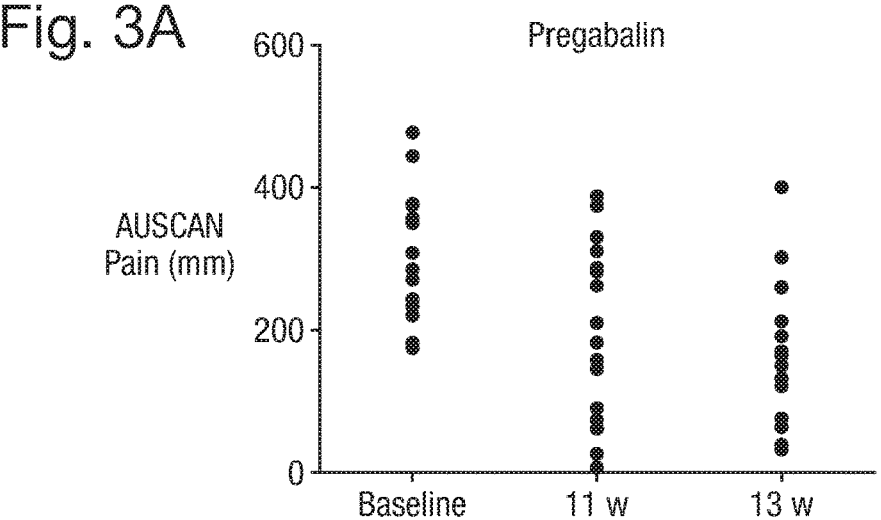
FIG. 3 shows graphs demonstrating the change in AUS-CAN pain, stiffness and function in the three treatment groups identified in Example 1.
Figure 3B:
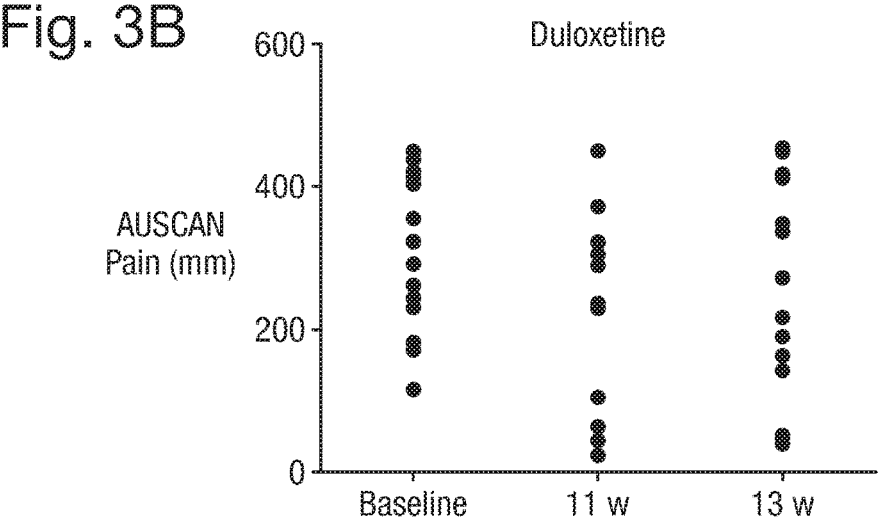
Figure 3C:
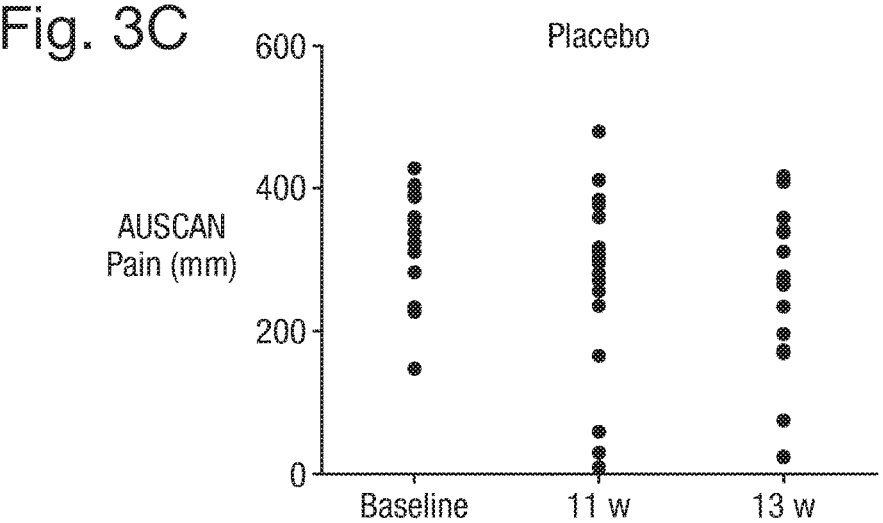
Figure 3D:
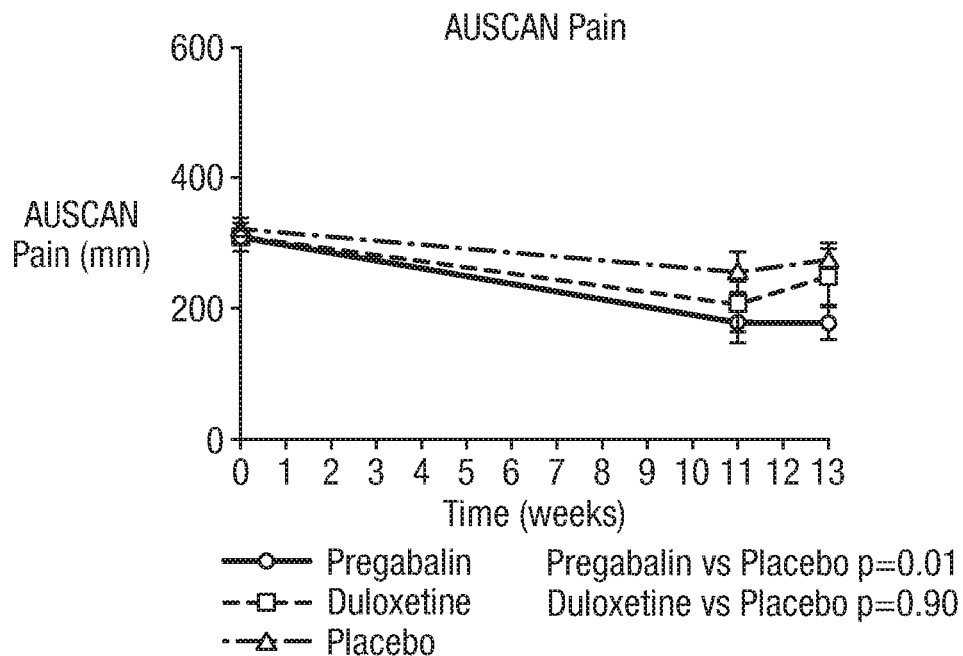
Figure 3E:
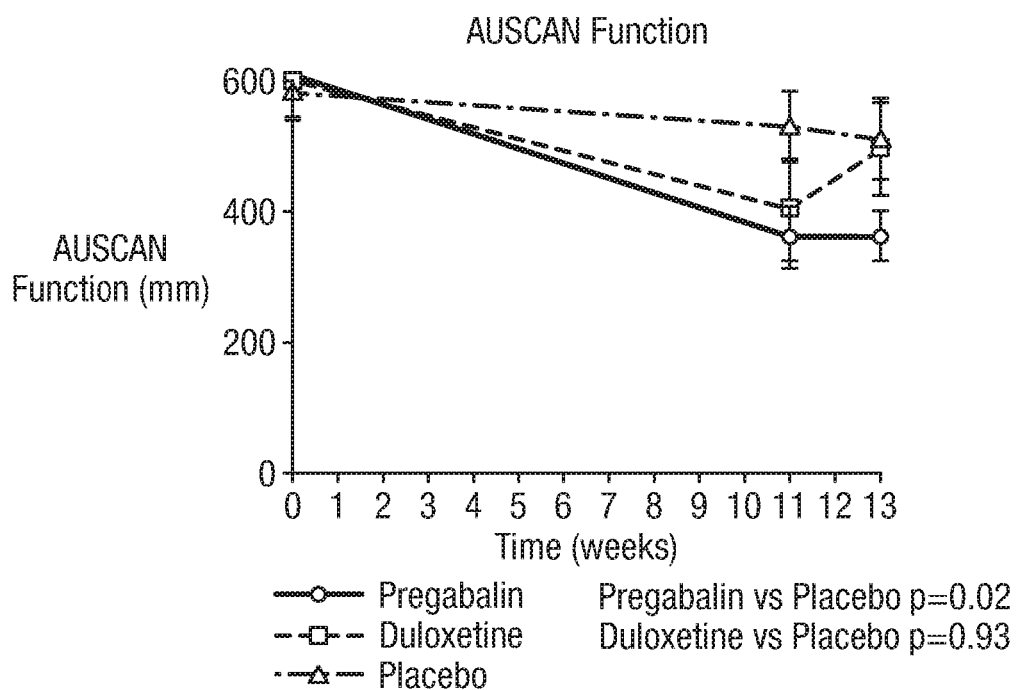
Figure 3G:
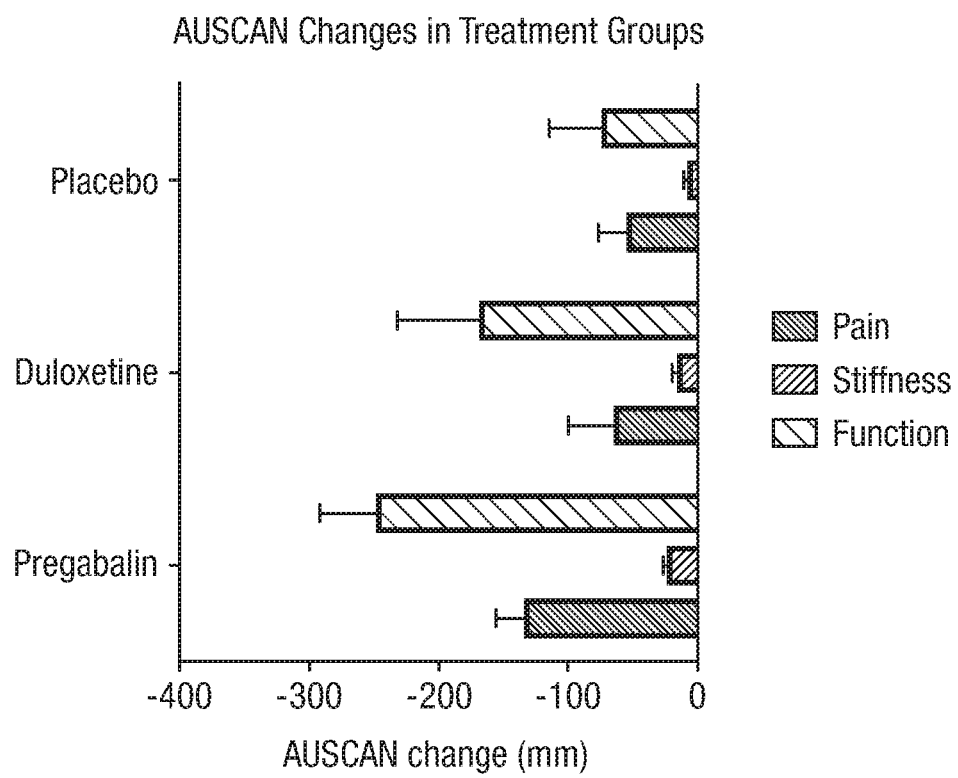
Figure 3G:
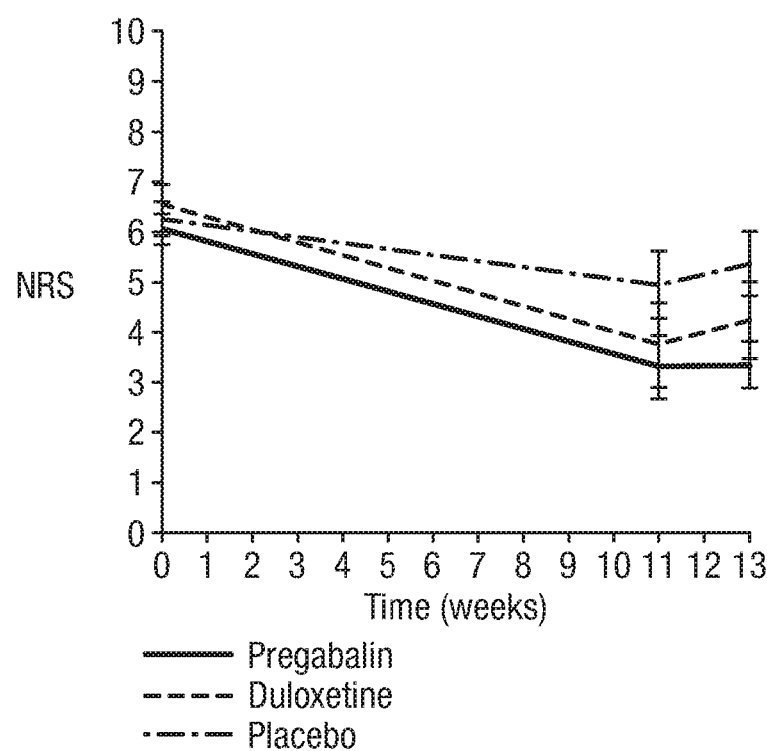

Between April 2013 and April 2016 85 participants were recruited into the study based on the CONSORT diagram (FIG. 2). A total of 21 participants were randomised to duloxetine, a further 22 to pregabalin and 22 to placebo respectively. There were 20 aged-matched non-hand OA participants enrolled. At enrolment, 56% of the trial participants had been taking regular paracetamol up to 4 g daily and 53% of the study group taking additional oral NSAIDs or opioid analgesics. All 65 participants who were randomised to treatment were included in the intention-to-treat analysis. A total of 42 participants completed the trial to the end of week 12 and were included in the per protocol analyses. The baseline characteristics of the study population demonstrates that all three treatment groups randomised to duloxetine, pregabalin and placebo were well-matched for age, body mass index, baseline AUSCAN pain score, and duration of diagnosis with no statistically significant difference between groups (Table 1).

TABLE 1

Baseline characteristics of study patients (values are numbers in percentages unless given otherwise)

| Characteristic | Pregabalin (n = 17) | Duloxetine (n = 16) | Placebo (n = 19) |
|---|---|---|---|
| Mean (SD) age (years) | 63.3 (4.6) | 61.1 (6.7) | 62.5 (9.1) |
| Women | 16 (94.1) | 12 (75.0) | 17 (89.5) |
| White | 15 (88.2) | 15 (93.8) | 15 (78.9) |
| Black | | | |
| Asian | 2 (11.8) | 1 (6.2) | 1 (5.3) |
| Other | | | 3 (15.8) |
| Mean (SD) Body mass index | 27.1 (6.4) | 27.3 (4.9) | 26.5 (3.9) |
| Mean AUSCAN pain score (SD) | 308.5 (89.4) | 310.6 (105.8) | 321.1 (67.2) |
| Mean Numerical Rating Scale (NRS) (SD) | 6.1 (1.2) | 6.6 (1.6) | 6.3 (1.4) |
| Mean Hospital Anxiety and Depression Scale (HADS) (SD) | 11.2 (7.5) | 9.7 (6.4) | 13.0 (5.8) |
| Most common analgesics before inclusion | | | |
| Paracetamol | 13 | 6 | 10 |
| Other NSAID oral/topical | 5 | 4 | 5 |
| Codeine based analgesic | 3 | 4 | 6 |
| Mean Duration of diagnosis in years (SD) | 21 (1.8) | 4.4 (4.6) | 5.8 (1.7) |

None of the participants enrolled had clinically significant levels of anxiety or depression. The three groups were well balanced, in terms of their demography as well as in clinical baseline characteristics. No formal tests were made in compliance with the CONSORT guidelines (Moher et al., J Clin epidemiol. 2010; 2010(63):e1-37). A total of 13 withdrawals occurred during the study (see Table 3 below).

Patient Reported Outcomes

Results for primary and secondary outcome measures are shown in Table 2.

TABLE 2

Primary and secondary outcomes in per-protocol population

| Outcome (imputed data on per protocol set) | Pregabalin | Duloxetine | Placebo |
|---|---|---|---|
| AUSCAN pain score | | | |
| Baseline (95% CI) | 308.5 (262.6 to 354.5) | 310.6 (254.3 to 367.0) | 321.1 (288.7 to 353.4) |
| 90 days (95% CI) | 176.5 (123.9 to 229.1) | 248.1 (162.3 to 333.9) | 273.5 (218.0 to 329.0) |
| Mean diff (95% CI) | −132.0 (−181.1 to −82.9) | −62.5 (−141.6 to 16.6) | −47.1 (−93.8 to 11.7) |
| P value | 0.01* | 0.9 | |
| AUSCAN stiffness | | | |
| Baseline (95% CI) | 59.9 (51.8 to 67.9) | 61.8 (45.8 to 77.8) | 56.1 (44.5 to 67.7) |
| 90 days (95% CI) | 36.5 (23.0 to 49.9) | 48.3 (29.9 to 66.6) | 50.0 (36.0 to 64.0) |
| Mean diff (95% CI) | −23.4 (−35.7 to −11.1) | −13.5 (26.5 to −0.6) | 5.7 (−16.8 to 5.5) |
| P value | 0.062 | 0.46 | |
| AUSCAN function | | | |
| Baseline (95% CI) | 608.5 (541.3 to 675.7) | 598.3 (481.2 to 715.3) | 580.0 (494.6 to 665.4) |
| 90 days (95% CI) | 362.2 (281.7 to 442.7) | 496.4 (342.4 to 650.5) | 508.7 (379.5 to 637.9) |
| Mean diff (95% CI) | −246.3 (−341.7 to −151.0) | −101.9 (−248.4 to −44.8) | −69.7 (−158.3 to −18.9) |
| P value | 0.02* | 0.93 | |
| Numerical Rating Scale (NRS) | | | |
| Baseline (95% CI) | 6.1 (5.4 to 6.7) | 6.6 (5.7 to 7.4) | 6.3 (5.6 to 6.9) |
| 90 days (95% CI) | 3.4 (2.4 to 4.4) | 4.3 (2.6 to 5.9) | 5.4 (4.1 to 6.6) |

TABLE 2-continued

Primary and secondary outcomes in per-protocol population

| Outcome (imputed data on per protocol set) | Pregabalin | Duloxetine | Placebo |
|---|---|---|---|
| Mean diff (95% CI) | −2.7 (−3.5 to −1.9) | −2.3 (−3.8 to −0.9) | −0.9 (−2.36 to 0.2) |
| P value | <0.0001* | 0.029* | 0.24 |
| Consumption of rescue medication (total) | 9 days | 5 days | 56 days |
| Hospital Anxiety and Depression Scale | | | |
| Anxiety | | | |
| Baseline (95% CI) | 6.1 (3.8 to 8.3) | 5.6 (3.6 to 7.5) | 7.6 (5.8 to 9.5) |
| 90 days (95% CI) | 5.2 (2.9 to 7.5) | 4.3 (2.2 to 6.3) | 8.2 (6.4 to 9.9) |
| Mean diff (95% CI) | −0.82 (−2.1 to 0.5) | −1.3 (−3.1 to 0.5) | 0.5 (−0.4 to 1.4) |
| P value | 0.52 | 0.21 | 0.71 |
| Depression | | | |
| Baseline (95% CI) | 5.1 (3.3 to 6.9) | 4.1 (2.3 to 5.9) | 5.4 (4.0 to 6.7) |
| 90 days (95% CI) | 4.1 (2.6 to 5.6) | 3.8 (1.9 to 5.7) | 5.1 (3.9 to 6.3) |
| Mean diff (95% CI) | −1.1 (−2.1 to −0.02) | −0.3 (−1.8 to 1.2) | 0.05 (−1.3 to 1.4) |
| P value | 0.41 | 0.54 | 0.93 |

For the primary outcome measure of AUSCAN pain, the mean difference in the pregabalin group between baseline and 13 weeks was −132.0 (95% confidence interval −181.1 to −82.9) compared with placebo of −47.1 (95% confidence interval −93.8 to 11.7), p=0.01. For the duloxetine group, the mean change in AUSCAN pain between baseline and 13 weeks was −62.5 (95% confidence interval −141.6 to 16.6) which was not significant compared with placebo, p=0.90.

For the secondary outcome measures, statistically significant results were found for the AUSCAN function outcomes in the pregabalin group compared with placebo between baseline and 13 weeks, p=0.02. The AUSCAN stiffness improvement did not reach statistical significance in the pregabalin group but showed a similar trend (p=0.06). Significant improvement in AUSCAN pain, stiffness or function were not observed in the duloxetine group compared with placebo. For the secondary outcome measure of NRS, pregabalin showed superior efficacy over placebo at 13 weeks (p<0.0001) as did duloxetine (p=0.029), demonstrating that both analgesics did have increased analgesic efficacy over placebo alone in hand OA. Pregabalin showed greater analgesic efficacy over placebo than duloxetine over placebo when considering AUSCAN pain outcomes and NRS. In addition, the analysis demonstrated that 32% of participants also had pain in other joint regions predominantly involving the knee and hip.

The average use of paracetamol as rescue medication was much lower in the pregabalin and duloxetine groups compared with placebo (Table 2). The use of rescue medication in the placebo group was significantly higher, amounting to a total of 56 days. Of note, there was no significant change in anxiety or depression scores in each of the three groups after treatment (Table 2). FIG. 3 demonstrates the trajectory in AUSCAN pain, stiffness and function outcomes in the pregabalin, duloxetine and placebo groups. Pregabalin demonstrated maximum analgesic and functional improvement effect at the higher dose of 300 mg, which was taken from week 2 to week 13. There was a trend towards a rise in pain reporting in the duloxetine and placebo groups between weeks 11 and week 13, which was not apparent in the pregabalin group.

Side Effect Profile

Side effects were common and recorded prospectively throughout the study for all participants (Table 3).

TABLE 3

Side effect profile in all three treatment groups

| System | Pregabalin | Duloxetine | Placebo |
|---|---|---|---|
| Cardiovascular | 3 | 2 | 1 |
| Digestive | 7 | 18 | 5 |
| ENT | | 2 | |
| Endocrine/Metabolic | 1 | | |
| Genitourinary | 1 | | |
| Haematological | | | |
| Mental | 9 | 9 | 9 |
| Nervous system | | | |
| Dry mouth | 6 | 6 | |
| Headaches | 3 | 8 | 4 |
| Dizziness | 7 | 3 | |
| Sleepiness | 5 | 3 | |
| Loss of balance | 7 | | |
| Ophthalmological | 4 | 2 | 1 |
| Respiratory | 2 | 3 | |
| Skin | | 1 | 2 |
| Total | 55 | 57 | 22 |

Withdrawals
Pregabalin: 1 family bereavement, 1 non-compliant, 1 lost to follow-up, 2 withdrew due to loss of balance
Duloxetine: 1 withdrew due to bronchitis, 4 withdrew due to gastrointestinal side-effects
Placebo: 3 withdrew from study due to non-compliance, 2 were lost to follow-up, 1 developed gastrointestinal side-effects The highest reporting of adverse events was observed in the pregabalin and duloxetine groups respectively: 55 adverse events were recorded with pregabalin, the most common of which were mental disturbance, headaches, sleepiness, dizziness and dry mouth with 4 participants having serious adverse events which resulted in discontinuation of the treatment before completing the trial. In the duloxetine group a total of 57 adverse events were recorded, requiring 2 participants to withdraw. The most common adverse events in the duloxetine group included digestive symptoms, mental disturbance and dry mouth. The placebo group showed fewer adverse events with a total of 22 recorded. There was no significant difference in adverse events between the 3 groups (p=0.73).

Pain Sensitisation

PPT testing was used as a quantitative measure for pain. Compared with non-OA controls, the hand OA group had reduced pain thresholds across all finger joints at baseline, even at the metacarpophalangeal joints and wrists where there was little evidence of radiographic OA (FIG. 4). Although there was some overlap in PPT values between controls and OA participants, overall as a group the PPT in the hand OA participants were significantly lower than the non-OA control group (p<0.0001). The pain thresholds did not improve after treatment in any of the 3 treatment groups (data not shown).

Discussion

Effective pain management is a therapeutic goal in OA and agents including paracetamol, which are recommended as first line analgesics, have been proven to be ineffective in recent large meta-analyses and trials (Da Costa et al., Lancet 2016; 387(10033): 2093-105; Williams et al., Lancet 2014; 384(9954): 1586-96). Therefore there is an unmet need for effective pain management in OA and the lack of new analgesic targets for OA in this most common arthritic disease prompted the present investigation into the use of the SNRI duloxetine and the gabapentinoid pregabalin. The two agents tested in the proof-of-concept study are as yet an under-explored therapeutic area in hand OA, since many phase III randomised trials focus on large joint OA of the hip and knee. The present trial of centrally-acting analgesics in hand OA has demonstrated an improvement in pain and function for pregabalin up to 300 mg daily for 12 weeks compared with duloxetine or placebo alone.

Pregabalin and duloxetine are both centrally acting agents; pregabalin is licensed for the treatment of neuropathic pain and duloxetine for the treatment of depression and diabetic pain. The present trial provides the first evidence in hand OA that pregabalin could be used as an effective analgesic for pain relief, including when other analgesics such as NSAIDs and even opiates as in some patients in our trial have proved ineffective. The trial demonstrated that at least half of participants were taking regular paracetamol and/or additional NSAIDs and opioids at the time of enrolment. Despite such high analgesic use, they were still reporting pain.

No reduction in pain or function on AUSCAN outcome measures for duloxetine and placebo was seen compared with pregabalin. Previous published trials (from the company marketing duloxetine) did show a therapeutic effect of duloxetine for pain, particularly in knee OA (Chappell et al., Pain 2009; 146(3): 253-60). There are several possibilities for this in the present study. Although no statistically significant improvement was seen over placebo for duloxetine using AUSCAN outcome measures, a significant difference was observed for the numerical rating scale NRS outcome measure, which was the most similar outcome measure to that used in the previous company-funded trial in knee OA. The AUSCAN pain scale was selected as the primary outcome measure in the present study since this is the most validated tool in hand OA trials (Bellamy et al., Arthritis Care Res (Hoboken) 2015; 67(7): 972-80). It is also possible that greater therapeutic analgesic effect may have been achieved at a higher dose of duloxetine 120 mg, but the maximum dose was not used in the present trial as it was a proof-of-concept study.

With respect to adverse effects, a higher frequency of side effects were observed in the pregabalin and duloxetine groups compared with placebo. Duloxetine at 60 mg demonstrated the highest frequency of side-effects related to the digestive system. For pregabalin, significant side-effects were observed at the dose of 300 mg, including dizziness, sleepiness, loss of balance and dry mouth. It is possible that future work to investigate the efficacy at lower doses of pregabalin may achieve similar analgesic effect with fewer side-effects.

Recent concepts in the development of novel therapeutic agents for OA have included targeting specific aspects of disease. These have included potential therapeutics for structural changes in the joint including synovitis (Kingsbury et al., Trials 2015; 16: 77) and bone marrow lesions (Bruyere et al. Drugs and Aging. 2015; 32(3): 179-187). However, such studies have not been without difficulty since recent trials targeting the inflammatory component of OA have not shown improved outcomes (Basoki et al., Ann Rheum Dis 2015; 74: 188) and the use of bisphosphonates potentially for reducing bone marrow lesions-related pain need to define significant clinical and structural end-points (Davis et al., PLOS ONE, 2013; 8(9):e72714).

There is a recent recognition of pain sensitisation, or a elevated phenomenon of pain sensitivity in people with OA (Wylde et al., Osteoarthritis Cartilage. 2011; 19(6): 655-8; Suokas et al., Osteoarthritis Cartilage 2012; 20(10): 1075-85; Neogi et al., Ann Rheum Dis. 2015; 74(4): 682-8). In the present trial quantitative sensory testing by PPT was used to evaluate participants with hand OA for pain sensitisation. The majority of the subjects had lower PPTs than non-OA controls at baseline and a significant reduction was found in AUSCAN and NRS pain scores in the pregabalin vs placebo group, with a reduction in NRS only in the duloxetine vs placebo group. However, PPT did not improve in any group after treatment, which may require further investigation in larger studies in the future.

Limitations

The proof of concept study used a pragmatic fixed dosing at mid-range therapeutic levels in order to evaluate a clinically-relevant treatment effect. Future studies would benefit from dose-ranging in a larger randomised trial of pregabalin with a dose-escalation design to establish the lowest doses at which efficacy may be demonstrated. Since this was a proof-of-concept analgesic endpoint study, structural outcome data including joint damage progression changes by plain radiography or synovitis by ultrasound were not collected, which could be addressed in future work.

Conclusions

The proof-of-concept study has compared the efficacy of pregabalin and duloxetine to placebo in a head-to-head trial. It has been demonstrated that the gabapentinoid pregabalin at a dose of 300 mg vs placebo daily shows superior efficacy to duloxetine 60 mg vs placebo in the treatment of hand OA pain. It has been identified that in patients who do not respond to usual care for OA pain including paracetamol, NSAIDs and opiates, pregabalin is more effective than placebo in participants with ongoing pain. No significant difference was observed in treatment between duloxetine and placebo for AUSCAN pain outcome. The study has also confirmed that hand held pressure algometry is a practical tool for pain testing in the clinic and can help identify sensitised patients who may respond to centrally-acting analgesics.

Recent work has suggested that OA pain can be stratified into distinct groups, including predominantly inflammatory phenotypes with synovitis and joint effusion and a sensitised phenotype. It is proposed that patients demonstrating a largely 'inflammatory' phenotype are more likely to respond to agents such as NSAIDs, whereas people who demonstrate features of sensitisation are more likely to respond to centrally acting agents such as pregabalin.

Example 2 (Brain Neuroimaging Component of the Study of Example 1)

Background

Chronic pain due to osteoarthritis (OA) may be aggravated by "central sensitisation", whereby pain processing pathways become sensitised by inflammatory and degenerative disease processes. 1H Magnetic Resonance Spectroscopy (MRS) and brain functional MRI (fMRI) were used to investigate whether there were biochemical changes in pain processing regions of the brain that could be related to perceived pain in patients with hand OA.

Further evaluation of people with hand OA in the study of Example 1 showed that a specific part of the brain, called the insula, showed higher signals relating to pain. The high brain pain signals were not seen in people who did not have arthritis.

Methods

MR acquisition: Data were acquired at 3T using PRESS single voxel localisation with TE 32 ms TR 2000 ms and 96 averages. Voxels were planned on 3D T1w images and placed in the anterior cingulate gyrus (voxel size 25×20×10 mm$^3$) and insula cortex (voxel size 25×10×15 mm$^3$). Metabolite levels were determined using LCModel™ as ratios to total creatine (tCr) to avoid the confound of CSF partial volumes. Data were only included for SNR>8 and CRLB<12% for the major metabolites of NAA, tCr, tCho, mI and Glx (Glu plus Gln).

Patients: Data were acquired on 32 hand OA patients (ages 49 to 76 yr) and 14 controls with no history of OA or chronic pain (ages 43 to 71 yr). Clinical scores were available for 22 patients as measured by visual analogue scale (VAS) for self-reported pain, painDETECT, the Australian and Canadian Hand Osteoarthritis Index (AUSCAN) and the Hospital Anxiety and Depression Scale (HADS).

Analysis: Statistical analyses were made with SPSS for linear correlations between MRS measures and clinical scores, Principal Component Analysis (PCA) with Varimax rotation, and a t-test for group comparisons.

Results

An initial group comparison was made with age-matched OA patients (63±5 yr), for which there was a significant difference in VAS pain scores (n=5 per group, VAS 5.2±4 and VAS 8±0.7 with p=0.0079). There was no significant difference in NAA/tCr or tCho/tCr between these groups. However Glx/tCr was reduced, mI/tCr was increased and mI/Glx was significantly increased in patients (0.34±0.03 v. 0.45±0.08, p=0.017) suggesting mI/Glx may be a useful biomarker relating to pain. Over the full age range, there were no metabolite differences found between controls and OA participants in the anterior cingulate gyrus or insula cortex. Also, there were no age related changes of metabolite ratios in either region in the controls or in the anterior cingulate gyrus of OA patients. However, in the insula cortex of OA patients the mI/Glx ratio was positively correlated with age (R2=0.29, p=0.0018, see FIG. 1) and with VAS pain score after co-varying for age (R2=0.52, p=0.018).

Since clinical scores of pain and related symptoms such as depression and anxiety are related, Principal Component Analysis (PCA) was performed across all clinical scores as a data reduction method to find which scores are related to MRS in the OA patient subgroup. Three PCs described 71% of the variance: PC1 was strongly weighted by AUSCAN pain and anxiety scores; PC2 by HADS anxiety and depression scores; PC3 by AUSCAN stiffness, painDETECT and VAS pain score. Using a ranked PC and mI/Glx correlation to minimise the effect of outliers, it was found that PC3 was correlated to mI/Glx (R2=0.188, p=0.049), with a stronger correlation after co-varying for age (R2=0.46, p=0.041).

Discussion

The correlation of insular cortex mI/Glx to PC3 of the clinical scores supports the hypothesis of this metabolite ratio being a biomarker relevant to perceived pain. However, how this metabolite ratio changes in relation to OA pain may not be straightforward, since in those age<65 yr, mI/Glx is lower in OA patients than controls, and for patients aged>65 yr there is elevated mI/Glx compared to controls. Increased myo-Inositol has been observed in neuro-inflammation and an increase in glutamate has been associated with acute pain stimulation. Hence there could be disease related changes in mI and Glx that are dependent on patient age and/or disease duration.

The invention claimed is:

1. A method of treating osteoarthritis in a patient in need thereof, wherein said patient is greater than or equal to 50 years old and has an elevated insular cortex mI/Glx ratio, the method comprises:
    (a) identifying said patient as being greater than or equal to 50 years old and having an elevated insular cortex mI/Glx ratio; and
    (b) administering to said patient an effective amount of pregabalin.

2. The method according to claim 1, wherein the osteoarthritis comprises hand osteoarthritis.

3. The method according to claim 1, wherein the method comprises administering the pregabalin as a single active agent.

4. The method according to claim 1, wherein the method comprises one, two or three of:
    (i) reducing joint pain in the patient;
    (ii) improving joint function in the patient; and
    (iii) reducing joint stiffness in the patient.

5. The method according to claim 1, wherein the patient is greater than or equal to 65 years old.

6. The method of claim 1, wherein said method does not comprise co-administering the pregabalin with meloxicam.

7. The method according to claim 1, wherein the patient has elevated pain sensitivity.

8. The method according to claim 7, wherein the method comprises reducing said elevated pain sensitivity.

9. The method according to claim 1, wherein the patient is greater than or equal to 55 years old.

10. The method according to claim 1, wherein the patient is greater than or equal to 60 years old.

11. The method according to claim 2, wherein the method comprises one, two or three of:
    (i) reducing hand pain in the patient;
    (ii) improving hand function in the patient; and
    (iii) reducing hand stiffness in the patient.

12. The method according to claim 2, wherein the patient suffers from osteoarthritis in at least one joint other than joints in the hand.

13. The method according to claim 2, wherein the patient suffers from at least one of knee osteoarthritis and hip osteoarthritis.

* * * * *